(12) United States Patent
Uyttersprot et al.

(10) Patent No.: US 10,344,252 B2
(45) Date of Patent: Jul. 9, 2019

(54) PROCESS FOR MAKING A LIQUID LAUNDRY DETERGENT COMPOSITION

(71) Applicant: The Procter & Gamble Company, Cincinnati, OH (US)

(72) Inventors: Jan-Sebastiaan Uyttersprot, Halle (BE); Walter August Maria Broeckx, Berlare (BE); Davinia Chantal Carine Brouckaert, Ghent (BE); Thomas Rogier Marc De Beer, Bachte (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/463,035

(22) Filed: Mar. 20, 2017

(65) Prior Publication Data
US 2017/0275573 A1    Sep. 28, 2017

(30) Foreign Application Priority Data
Mar. 24, 2016 (EP) .................................. 16162424

(51) Int. Cl.
| | |
|---|---|
| *C11D 11/00* | (2006.01) |
| *C11D 3/37* | (2006.01) |
| *C11D 1/22* | (2006.01) |
| *G01N 21/65* | (2006.01) |
| *G01N 21/85* | (2006.01) |
| *C11D 17/04* | (2006.01) |
| *G01N 21/84* | (2006.01) |

(52) U.S. Cl.
CPC ............ *C11D 11/0017* (2013.01); *C11D 1/22* (2013.01); *C11D 3/3723* (2013.01); *C11D 11/0023* (2013.01); *C11D 11/0094* (2013.01); *C11D 17/043* (2013.01); *G01N 21/65* (2013.01); *G01N 21/85* (2013.01); *G01N 2021/8416* (2013.01); *G01N 2201/06113* (2013.01)

(58) Field of Classification Search
CPC ... C11D 11/0017; C11D 11/0023; C11D 1/22; C11D 3/3723; C11D 17/043
See application file for complete search history.

(56) References Cited

U.S. PATENT DOCUMENTS

| | | | | |
|---|---|---|---|---|
| 4,568,354 A | * | 2/1986 | Davis ........................ | C10L 1/10 44/302 |
| 4,568,355 A | * | 2/1986 | Davis ...................... | C10L 1/023 44/302 |
| 4,608,057 A | * | 8/1986 | Davis ...................... | C10L 1/328 44/281 |

(Continued)

FOREIGN PATENT DOCUMENTS

| | | | |
|---|---|---|---|
| CN | 1234865 A | * | 11/1999 |
| JP | 2013170873 A | * | 9/2013 |

OTHER PUBLICATIONS

JP 2013 170873. English Translation. Ishakawa et al.*

(Continued)

*Primary Examiner* — Nicole M. Buie-Hatcher
*Assistant Examiner* — M. Reza Asdjodi
(74) *Attorney, Agent, or Firm* — Gregory S. Darley-Emerson

(57) ABSTRACT

A process for making a liquid detergent composition, the process including a step of passing the liquid detergent composition via Raman Spectroscopy apparatus.

17 Claims, 1 Drawing Sheet

(56) References Cited

U.S. PATENT DOCUMENTS

| | | | | |
|---|---|---|---|---|
| 6,100,975 | A * | 8/2000 | Smith | G01J 3/02 356/301 |
| 6,514,767 | B1 * | 2/2003 | Natan | G01N 21/658 356/301 |
| 6,861,263 | B2 * | 3/2005 | Natan | G01N 21/658 356/301 |
| 7,192,778 | B2 * | 3/2007 | Natan | B22F 1/0018 436/166 |
| 7,443,489 | B2 * | 10/2008 | Natan | B22F 1/0018 356/36 |
| 8,932,400 | B2 * | 1/2015 | Chen | C04B 28/02 106/713 |
| 2003/0124028 | A1 * | 7/2003 | Carlson | B01J 19/0046 422/68.1 |
| 2003/0163953 | A1 * | 9/2003 | Hazel | C10L 1/023 44/412 |
| 2003/0217505 | A1 * | 11/2003 | Maubert | C10L 1/143 44/388 |
| 2006/0054506 | A1 * | 3/2006 | Natan | B22F 1/0025 205/112 |
| 2007/0019191 | A1 * | 1/2007 | Marrow | B01J 19/0006 356/301 |
| 2007/0021586 | A1 * | 1/2007 | Marrow | B01J 19/0006 528/363 |
| 2008/0165354 | A1 * | 7/2008 | Rantanen | G01N 13/00 356/301 |
| 2008/0180661 | A1 | 7/2008 | Brown et al. | |
| 2013/0085680 | A1 * | 4/2013 | Arlen | G01N 27/44756 702/19 |
| 2014/0118731 | A1 * | 5/2014 | Ayers | G01J 3/0237 356/301 |
| 2014/0170763 | A1 * | 6/2014 | Williams | G01N 21/65 436/140 |

OTHER PUBLICATIONS

Gaubert et al. Laundry detergent formulation. Analytica Chemica Acta. 915 (2016) 36-48.*

Research Disclosure, Quest Irland LTD (Year: 2004).*

Gaubert Alexandra et al: "Characterization of surfactant complex mixtures using Raman spectroscopy and signal extraction methods: Application to laundry detergent deformulation", Analytica Chimica Acta, vol. 915 , pp. 36-48, XP029462021, ISSN: 0003-2670, 001: 10.1 016/J.ACA.2016.02.016.

European Search Report for Application No. 16162424.2-1375, dated May 5, 2016, 7 pages.

* cited by examiner

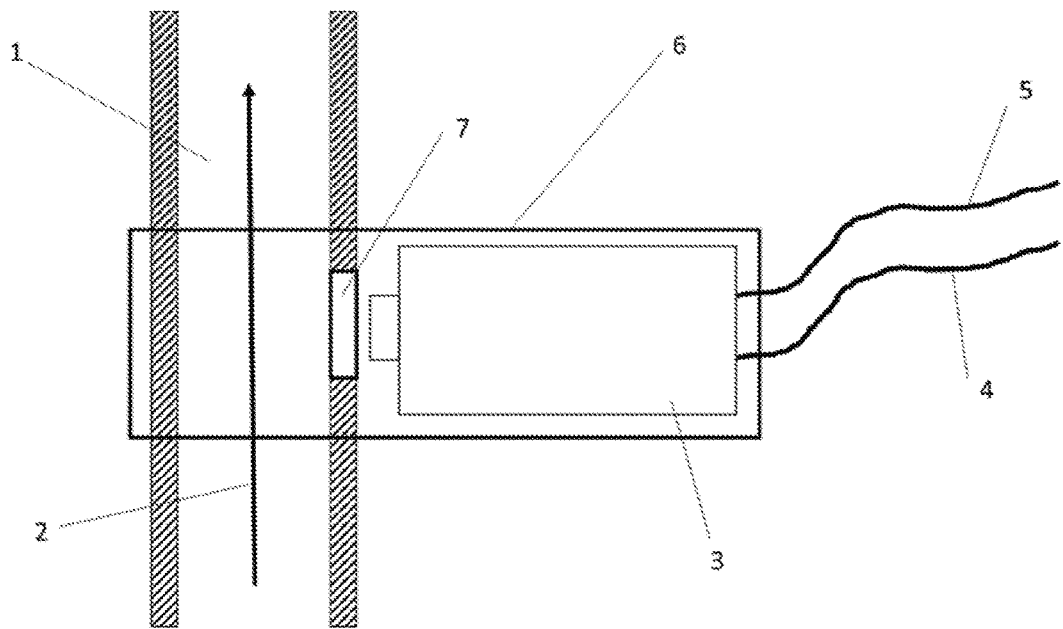

PROCESS FOR MAKING A LIQUID LAUNDRY DETERGENT COMPOSITION

FIELD OF THE INVENTION

The present disclosure relates to a process for making a liquid detergent composition wherein the process comprises a step of passing the liquid detergent composition via Raman Spectroscopy apparatus.

BACKGROUND OF THE INVENTION

Manufacture of liquid detergent compositions requires careful balance of ingredients and process steps. During manufacture aspects of the process may need to be adjusted, for example to add more of a particular ingredient or adjust the pH of the composition, to ensure it meets product specifications. If the final product does not meet preferred specifications, this could negatively impact the cleaning or care ability of the composition and so negatively affect the consumer experience. Further it could negatively impact factors such as physical stability or physical state of the product (viscosity, pH, color etc), odor profile, safety profile or regulatory compliance. Again these can negatively affect the consumer experience.

Traditionally, during the manufacturing process samples are collected and analyzed to ensure the product meets specification. If it does not then it can be adjusted by addition of relevant components or ingredients, or the product is recycled back to make adjustments, or in some cases the product needs to be scrapped which is expensive and inefficient. However, such process does not allow for 'real-time' adjustment. This is inefficient as by the time the error has been noticed, the product has already moved down the production line and needs to be recycled back, or it has to be held in a storage tank until the relevant adjustment has been made. This affects process throughput as a continuous process cannot be run where a storage tank is required ahead of release of the product. Similarly, traditional methods do not allow early trend identification and hence fast interception to prevent product that does not meet specifications. All of this can be resource intensive both from a cost and 'manpower' perspective.

Also, traditionally only one characteristic at a time is measured, for example, pH or conductivity or weight percentage of one particular ingredient. This is again inefficient as a number of different measurement devices need to be used one after another to check all relevant characteristics.

Therefore, there is a need in the art for a continuous process to make a liquid detergent composition wherein the characteristics of the composition can be adjusted in real-time and more efficiently than using current techniques.

SUMMARY OF THE INVENTION

The present disclosure relates a process for making a liquid detergent composition comprising the steps of:
a. Flowing a liquid detergent composition through a pipe, wherein the liquid detergent composition comprises two or more detergent ingredients;
b. Flowing the liquid detergent composition through the pipe via a Raman Spectroscopy apparatus, wherein the Raman Spectroscopy apparatus comprises a probe, and wherein the Raman Spectroscopy apparatus periodically scans the liquid detergent composition via the probe;
c. Interpreting the scanned data to determine levels of one or more of the detergent ingredients present in the liquid detergent composition;
d. Comparing the levels of the detergent ingredients present in the liquid detergent composition to pre-determined acceptable level ranges for said ingredients;
e. Optionally adjusting the level of one or more detergent ingredients, preferably by addition of one or more detergent ingredients to the liquid detergent composition;
f. Flowing the liquid detergent composition to where optionally one or more further process steps occur;
g. Collecting the liquid detergent composition.

The present disclosure also relates to the use of Raman Spectroscopy to levels of one or more detergent ingredients present in a liquid detergent composition during a manufacturing process, preferably a continuous manufacturing process to make said liquid detergent composition.

The present disclosure also relates to the use of Raman spectroscopy to anticipate a trend towards the level of one or more detergent ingredients within a liquid detergent composition becoming outside of pre-determined level ranges during the manufacture of the liquid detergent composition, whereby such anticipation triggers an auto-correction step to prevent the one or more ingredient levels becoming out of pre-determined level ranges.

BRIEF DESCRIPTION OF THE DRAWINGS

FIG. 1 discloses schematic of the process according to the present disclosure.

DETAILED DESCRIPTION OF THE INVENTION

Process

The present disclosure relates to a process for making a liquid detergent composition. In relation to the liquid detergent composition of the present disclosure, the term 'liquid' encompasses forms such as dispersions, gels, pastes and the like. A dispersion for example is a liquid comprising solid or particulate matter contained therein.

The liquid composition may also include gases in suitably subdivided form. However, the liquid composition excludes forms which are non-liquid overall, such as tablets or granules.

The term 'detergent composition' includes any composition capable of wetting or treating a surface, wherein the surface could be flexible, e.g. a fabric, or hard, e.g. a floor or kitchen unit. The detergent composition may comprise a fabric laundry or softening detergent composition, a hard surface cleaner, a hand dishwashing liquid, an automatic dishwashing composition or a combination thereof.

The liquid detergent composition is preferably selected from laundry detergents, hard surface cleaners, dish washing detergents or mixtures thereof, preferably wherein the liquid detergent composition is a liquid laundry detergent composition. The liquid detergent composition is described in more detail below.

The liquid detergent composition may be used as a final product sold to consumers or may be an intermediate composition which is further processed to make a final product for sale to consumers.

Step a: The process comprises a step of a flowing liquid detergent composition through a pipe, wherein the liquid detergent composition comprises two or more detergent ingredients. The liquid detergent composition is described in more detail below.

The pipe is used to flow the liquid detergent composition through the manufacturing apparatus to a collection point. The pipe can be of any suitable material or construction and those skilled in the art will recognise suitable structures and materials. The pipe has to be suitable for the flow of the liquid detergent composition, and be of sufficient size to achieve a flow of liquid detergent composition to achieve desired manufacturing throughput. It is also preferred that the diameter and internal volume of the pipe is sufficient to minimise blockages of the liquid detergent composition and will be dependent on the chemical make-up of the liquid detergent composition, e.g. viscosity, presence of particulates etc. Those skilled in the art will be aware of relevant pipe diameters and volumes dependent on chemical nature of the liquid detergent composition.

The pipe may be constructed from any suitable material. Those skilled in the art will be aware of suitable materials. The pipe may be constructed from metal, plastic or a mixture thereof. Suitable metals include stainless steel, carbon steel or a mixture thereof. Stainless steel may be selected from commercially available grades 316, 316L, 304, 304L or a mixture thereof. Carbon steel may be selected from commercially available CS-1018, Carpenter 20-CB3, 2205, AL6XN, Hastelloy C-276 or mixtures thereof. Preferably the pipe is constructed of stainless steel. Suitable plastics include, polypropylene, chlorinated polyvinylchloride, Teflon TFE, Fiber Reinforced Plastic (FRP) or a mixture thereof. Suitable FRP includes Derakane 411M.

It is also preferable that the pipe is constructed such that addition of other materials and/or process steps can be achieved to the liquid detergent composition as it is flowing through said pipe. For example, it is preferable that the pipe comprises one or more inlet valves within the wall of the pipe to allow addition of further ingredients commonly used in detergent compositions. It may be desirable to add certain ingredients up or down stream of the addition of other ingredients, for reasons of compatibility or mixing requirements.

The pipe may comprise one or more mixing elements. Those skilled in the art will be aware of suitable mixing elements. The mixing element may be selected from static mixers, dynamic mixers or a mixture thereof. The mixing element may be in the form of a small mixing tank such as a continuous stirred reactor.

Step b: The process comprises a step b of flowing the liquid detergent composition through the pipe via a Raman Spectroscopy apparatus, wherein the Raman Spectroscopy apparatus comprises a probe, and wherein the Raman Spectroscopy apparatus periodically scans the liquid detergent composition via the probe. The Raman Spectroscopy apparatus is described in more detail below.

Without wishing to be bound by theory, Raman Spectroscopy is a technique whereby inelastic scattering of monochromatic light is used to determine the vibrational modes of molecules in a system. It can be used to provide information on the molecules present in a particular system by comparing the data obtained to that of a standard. It has the added benefit of providing information on the presence of multiple molecules present in the same system at the same time, so a vast array of information regarding the make-up of a particular composition can be obtained using a single sensor. Another advantage is that water only has a very weak response in Raman which makes it very useful to quantify actives dissolved into water without facing an overwhelming water signal due to its dominant presence inside the liquid detergent composition. This would be much more difficult with infrared spectroscopy, i.e. where the water signal would dominate the spectrum and as such rendering it a challenge to quantify the vast majority of dissolved substances. In addition the process of the present disclosure allows fast measurements, which is especially useful in continuous processes.

The liquid detergent composition is periodically scanned. A single scan of the liquid detergent composition as it flows via the Raman Spectroscopy apparatus can be achieved within 0.4 seconds. Periodic scans can be performed on any preferred frequency. Preferably, the liquid detergent composition is scanned between every 0.4 and 120 seconds, more preferably between every 1 and 60 seconds.

The Raman apparatus may be positioned in any suitable point along the pipe. Those skilled in the art will recognise suitable positions. The Raman apparatus may be positioned along a section of pipe comprising no inlet valves or mixing elements. Alternatively, the Raman apparatus may be positioned along a section of pipe comprising a mixing element wherein the mixing element is described as above.

Step c: The process comprises a step c of interpreting the scanned data to determine levels of one or more of the detergent ingredients present in the liquid detergent composition. The data obtained from scanning the liquid detergent composition is compared to standards in order to determine the levels of one or more of the detergent ingredients in the liquid detergent composition. Preferably, the detergent ingredients comprise polymers, surfactants, builders, solvents or a mixture thereof. For example, upon comparison to a standard, it is possible to determine the weight percentage of a particular ingredient present in the liquid detergent composition.

Preferably the interpretation of the data is done via an automated system, most preferably via computer software. The computer software will utilize an algorithm in order to determine the levels of the detergent ingredients based on standards that have previously been scanned and interpreted. Those skilled in the art will be aware of relevant computer software and algorithms that can be used to achieve this.

Step d: The process comprises a step d of comparing the levels of the detergent ingredients present in the liquid detergent composition to pre-determined acceptable level ranges for said detergent ingredients. Without wishing to be bound by theory, the 'acceptable ranges' are pre-determined by the manufacturer based on known levels of ingredients in control compositions. If the concentration of a particular ingredient is outside of the range this can be alerted as an action in order to correct the deviation.

Preferably, the comparison is done via an automated system, most preferably via computer software. The computer software will use an algorithm to determine whether the levels of one or more of the detergent ingredients are within or outside of acceptable ranges. When outside of the acceptable ranges, the software can alert the manufacturer, by for example displaying a warning on an apparatus control screen. The software may also indicate what action needs to be taken to correct the issue and bring the detergent ingredient levels back within acceptable ranges. The manufacturer can then take the appropriate corrective action. Alternatively, the software may enact an automatic corrective action, in other words, if a particular level is identified as outside of the acceptable ranges, the software will automatically instruct the manufacturing apparatus to take the necessary action to correct this either with or without an alert to the manufacturer. The correction can happen at any point downstream or upstream of the Raman Spectroscopy apparatus in the production line.

Step e: The process comprises a step e of optionally adjusting the level of one or more detergent ingredients, preferably by addition of one or more detergent ingredients to the liquid detergent composition. From step d it will be known whether the levels of one or more detergent ingredients of the liquid detergent composition are within or outside of the acceptable ranges. The manufacturer can then, based on this information, add further ingredients to the liquid detergent composition necessary to bring it back within acceptable ranges.

As detailed in step d, the addition of one or more ingredients can be done manually or automatically. Manual addition can be achieved by computer-enabled control, i.e. a command is entered via a relevant computer software which actuates nozzles, pumps, valves and the like to add a desired quantity of the one or more ingredients to the liquid detergent composition. Alternatively, the manufacturer can manually activate relevant nozzles, pumps and valves without computer-enabled control.

Alternatively, following step d the addition of the one or more ingredients can be achieved automatically. In which case, the computer software automatically instructs the nozzles, pumps, valves and the like to add the relevant volume of one or more ingredients to return the detergent ingredient levels to within the acceptable ranges.

Addition of the one or more ingredients can be done downstream or upstream of the Raman Spectroscopy apparatus. If the one or more ingredients is added downstream of the Raman Spectroscopy apparatus this will allow correction of levels of the detergent ingredients of the liquid detergent composition that has just been scanned. Alternatively, addition of detergent ingredients upstream can be used to correct a 'trend' towards the liquid detergent composition being outside of the acceptable ranges. In other words, the addition of detergent ingredients upstream results in the liquid detergent composition at the point of collection being within acceptable ranges. It also has the added benefit that that since addition will be upstream of the Raman Spectroscopy Apparatus the liquid detergent composition can be checked to ensure that the addition has resulted in the formulation characteristics returning to within acceptable ranges. Alternatively, if liquid detergent composition comprising one or more detergent ingredients at a level outside of acceptable ranges is collected, e.g. in a storage tank, then correction upstream of the liquid detergent composition means that as more liquid detergent composition is collected then as it mixes in the storage tank the levels outside of acceptable ranges will be altered/corrected.

Alternatively, if the level of one or more detergent ingredients are not within acceptable ranges then the liquid detergent composition can be diverted via 'correction loop' or the like whereby the necessary addition of one or more ingredients is made ahead of the diverted liquid detergent composition rejoining the liquid detergent composition up- or downstream of the Raman Spectroscopy apparatus.

Adjustment by addition of one or more detergent ingredients to the liquid detergent composition occurs upstream of the Raman spectroscopy apparatus, downstream of the Raman spectroscopy apparatus, via a correction loop or a mixture thereof.

The one or more ingredients can be added to the liquid detergent composition via any suitable means. The one or more ingredients may be added via an inlet to the pipe through which the liquid detergent composition is flowing.

For example, an ingredient may be located in a ancillary storage tank which is connected to the pipe by a recloseable inlet. The recloseable inlet may be a valve or nozzle which can be opened as desired to allow a suitable volume of the ingredient to flow into the pipe and mix with the liquid detergent composition. Those skilled in the art will be aware of suitable means to add the one or more ingredients.

Preferably, the optional addition of further ingredients to adjust the level of one or more detergent ingredients in the liquid detergent composition occurs within 30 seconds, preferably within 20 seconds, more preferably within 10 seconds of the comparison in step d.

Step f: The process comprises a step f of flowing the liquid detergent composition to where optionally one or more further process steps occur. Those skilled in the art will be aware of relevant further process steps. Such steps could include addition of further ingredients, mixing, heating of the composition, cooling of the composition, or a mixture thereof. The addition of further ingredients in step f preferably includes acidic or alkali materials to adjust pH, viscosity adjustment agents, aesthetic dyes, perfumes, preservatives or a mixture thereof. Mixing steps could include passing the liquid detergent composition through a low or high shear static mixer, a low or high shear dynamic mixer or a mixture thereof.

Step g: The process comprises a step g of collecting the liquid detergent composition. The collected liquid detergent composition may be used as a fully formulated consumer product or may serve as an intermediate product. If it is an intermediate product, then one or more further ingredients and/or process steps may be applied to the liquid detergent composition in order to result in a fully formulated consumer product.

Without wishing to be bound by theory, a further benefit of the present disclosure is that from a product quality standpoint, product may be 'released for sale' quicker, even in real time. Often manufactured product needs to be checked to ensure it meets certain manufacturing quality standards (e.g. levels of ingredients within pre-determined ranges) before it is permitted by the manufacturer to be sold to consumers. Often times such verification is done once the product is made. This means there is an additional step of storing the product ahead of it being released. This is time and cost ineffective. Since the process of the present disclosure achieves this during manufacture, product can be released quicker or even 'real time', i.e. at the point the manufacturing steps have been completed.

The liquid detergent composition may be collected into any suitable container. Those skilled in the art will be aware of appropriate containers. The liquid detergent composition may be collected in a bottle, a tub, a water-soluble unit dose article, a holding tank or a mixture thereof. Suitable containers are described in more detail below.

The process may be a continuous process, a batch process or a semi-continuous process, preferably the process is a continuous process.

A batch process is a process whereby a pre-determined volume of product is manufactured in an isolated system. Once a particular batch is made, it is removed from the system and a new batch is then started. This means there is a period of time between batches whereby no product is being manufactured. In a continuous process, materials are added constantly and product is manufactured and collected continuously. Unlike batch processes there is no interruption between when product is being manufactured.

A semi-continuous process is more where the process can be interrupted, for example have an intermediate storage stage but wherein the overall process per se is continuous.

Without wishing to be bound by theory, the specific use of Raman Spectroscopy apparatus enables a continuous process as scanning and correction of multiple ingredient levels can be simultaneously achieved in real time.

Preferably, the liquid detergent composition is flowing at rate of between 5000 kg per hour and 150,000 kg per hour.
Liquid Detergent Composition The liquid detergent composition comprises two or more, preferably three or more detergent ingredients. In other words, the detergent composition does not comprise a single detergent ingredient, rather it comprises at least two different detergent ingredients. Suitable detergent ingredients are described in more detail below.

In the context of the present disclosure, a liquid detergent composition is a composition whereby at least two detergent ingredients are present in liquid form. A detergent ingredient is any ingredient commonly used in a liquid detergent. The detergent ingredient may provide a cleaning benefit, a shine benefit, a softness benefit, a freshness benefit, a preferred viscosity, a preferred pH, a preferred color or a mixture thereof. Water may be a detergent ingredient. However, the liquid detergent composition should not be understood to be made solely from one ingredient.

The liquid detergent composition is preferably selected from laundry detergents, fabric enhancers, hard surface cleaners, air care refreshers, dish washing detergents or mixtures thereof, preferably wherein the liquid detergent composition is a liquid laundry detergent composition.

The liquid detergent composition may be used as a fully formulated consumer product or may serve as an intermediate product. If it is an intermediate product, then one or more further ingredients and/or process steps may be applied to the liquid detergent composition was collected in step g of the present process in order to result in a fully formulated consumer product.

The detergent ingredients may be mixed together in any suitable order in order to make the liquid detergent composition. The ingredients may all be mixed together and then flowed through the pipe or some of the ingredients may be initially mixed together and then flowed through the pipe after which further ingredient or ingredients are added whilst the liquid detergent composition is in transit through the pipe. Those skilled in the art will know appropriate order of mixing.
Detergent Ingredients The detergent ingredient may be selected from any ingredient commonly used in a liquid detergent composition. Those skilled in the art will be aware of suitable ingredients.

The detergent ingredient may be selected from surfactants, builders, chelants, polymers, organic solvents, inorganic solvents, dyes, perfumes, preservatives, antibacterial agents, viscosity modifiers, pH adjustment agents, water or a mixture thereof.

Preferably, the detergent ingredient may be selected from surfactants, builders, polymers, organic solvents, water or a mixture thereof.
Container The liquid detergent composition may be collected in step g in a bottle, a tub, a water-soluble unit dose article, a holding tank or a mixture thereof.

The liquid detergent composition may be collected in a bottle. Preferably, the liquid detergent composition is flowed via a nozzle into the bottle, after which the bottle is closed. Those skilled in the art will be aware of suitable nozzles to achieve this. The bottle may be of any shape and volume. Those skilled in the art will be aware of suitable shapes and volumes for the bottle.

The liquid detergent composition may be collected in a water-soluble unit dose article. Preferably, a first water-soluble film is deformed in a mould to form an open cavity. The liquid detergent composition is then added to the open cavity preferably via a nozzle. A second water-soluble film is then used to close the open cavity containing the liquid detergent composition, and the first and second films are then sealed together preferably via heat, solvent or a mixture thereof.

The water-soluble unit dose article comprises at least one water-soluble film shaped such that the unit-dose article comprises at least one internal compartment surrounded by the water-soluble film. The at least one compartment comprises the liquid detergent composition. The water-soluble film is sealed such that the liquid detergent composition does not leak out of the compartment during storage. However, upon addition of the water-soluble unit dose article to water, the water-soluble film dissolves and releases the contents of the internal compartment into the wash liquor.

The unit dose article may comprise more than one compartment, even at least two compartments, or even at least three compartments. The compartments may be arranged in superposed orientation, i.e. one positioned on top of the other. Alternatively, the compartments may be positioned in a side-by-side orientation, i.e. one orientated next to the other.

Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. Suitable water soluble films are commercially available from Monosol.

The liquid detergent composition may be collected in a holding vessel. The holding vessel may be used to temporarily or permanently store the liquid detergent composition. The liquid detergent composition may be temporarily stored in the holding vessel ahead of it being further processed or packaged into a relevant container. The holding vessel can be made from any suitable material and can have suitable dimension. Those skilled in the art will know suitable materials and dimensions.
Raman Spectroscopy Apparatus Raman Spectroscopy is a technique whereby inelastic scattering of monochromatic light is used to determine the vibrational modes of molecules in a system. It can be used to provide information on the molecules present in a particular system by comparing the data obtained to that of a standard. Those skilled in the art will know suitable Raman Spectroscopy apparatus.

Without wishing to be bound by theory, Raman Spectroscopy has the ability to measure active concentrations of ingredients in compositions comprising high levels of water. Water has only a weak response in Raman Spectroscopy where for other techniques like Fourier transform infrared spectroscopy (FT-IR) or near infrared it can strongly dominate the spectral response. Hence, when using Raman Spectroscopy the water signal will not overwhelm the signals of other ingredients. Raman has the additional advantage over FT-IR that it is more compatible with a manufacturing environment because it allows the use of remote probes via fibre-optic waveguides. Compared to Near Infrared it has the advantage that it has much higher chemical specificity in the spectral features.

The instrumentation for the inline measurement of Raman spectra comprises three main parts that can be physically separated and connected via optical fibers. These three components are the laser, the probe and the detector.

The laser plays an important role in the performance of a Raman spectrometer, including its sensitivity and stability. Two important parameters of the excitation source are its bandwidth and power. The laser emits monochromatic radiation in the ultra violet, visible and or near infra red region. Generally, the excitation source is selected according to the specific application. This is because the excitation bands of most fluorophores are in UV or visible wavelength regions. Therefore, excitation from a longer wavelength, such as in the NIR region, reduces the probability to excite fluorescence signals because of the lower photon energy The probe that ensures that the laser light is positioned correctly and the responding measured signal is directed to the detector.

The Raman spectrometer collects the measured signal via the detector and converts it into a measured response. In a typical Raman spectrometer, the Raman scattered light is dispersed using a diffraction grating, and this dispersed light is then projected onto the long axis of a charge-coupled device array (CCD). Without wishing to be bound by theory, the diffraction grating is an array of finely spaced lines on a reflective surface. It is used to split the light beam that comes from the sample into its constituent wavelengths.

A CCD is an electronic device, such as an electronic chip, that turns a photographical image into an electrical signal.

Those skilled in the art will know suitable lasers, probes and detectors.

The probe is located within the pipe, located external to the pipe of a mixture thereof, preferably wherein the probe is located external to the pipe. Without wishing to be bound by theory, the Raman Spectroscopy apparatus can scan the composition without the probe being present within the composition.

Preferably, the probe is located external to the pipe, and the pipe comprises a transparent region. The probe is located adjacent to said transparent region. Without wishing to be bound by theory, the probe can scan the base composition through the transparent region.

Preferably, the transparent region comprises sapphire, glass, quartz or a mixture thereof.

Without wishing to be bound by theory, a negative of probes within the liquid detergent composition is the risk of 'dead corner' creation where product might start to accumulate. Furthermore, constant contact of the probe with the liquid detergent composition can cause wear against the probe making it more prone to damage and hence replacement. If the probe is within the liquid detergent composition, it is also more difficult to replace i.e. requires stopping of production, whereas a probe located external to the pipe allows continuation of production with only temporary absence of analysis during probe replacement.

The probe may be enclosed within an enclosure in order to shield it from ambient light which may interfere with the measurement.

Use of Raman Spectroscopy

Another aspect of the present disclosure is the use of Raman Spectroscopy to determine levels of one or more detergent ingredients present in a liquid detergent composition during a manufacturing process, preferably a continuous manufacturing process to make said liquid detergent composition. Preferably, the use comprises an auto-correction step to correct the level of one or more detergent ingredients present in said liquid detergent composition following use of the Raman Spectroscopy to measure said levels. The process and liquid detergent compositions are according to the present disclosure.

Yet another aspect of the present disclosure is the use of Raman spectroscopy to anticipate a trend towards the level of one or more detergent ingredients within a liquid detergent composition becoming outside of pre-determined level ranges during the manufacture of the liquid detergent composition, whereby such anticipation triggers an auto-correction step to prevent the one or more ingredient levels becoming out of pre-determined level ranges. The process and liquid detergent compositions are according to the present disclosure.

EXAMPLES

FIG. 1 discloses a liquid detergent manufacturing process comprising a Raman Spectroscopy apparatus. In more detail, the liquid detergent composition flows through the pipe (1) is a single direction (2). The probe (3) is positioned outside of the pipe (1) and comprises a first optical fiber connecting it to the detector (4) and a second optical fiber connecting the laser to the probe (5). The pipe (1) comprises a transparent region (7) and the probe (3) is positioned adjacent to said transparent region (7). In the set-up of this example, the probe is also enclosed in an enclosure (6) to shield it from ambient light that could interfere with the measurement.

Example 1

An apparatus is set up according to FIG. 1.

The Raman Spectroscopy apparatus is set up with a CCD, Typical Spectral range: 250-3200 cm−1, Number of Pixel: 2048 (2D sensor), NIR enhanced Si sensor, Deep cooled sensor −50° C. for low noise measurement, Spectral resolution w/p: <2 cm−1, Optical spectral resolution 8 cm−1, Temperature range: 10-30° C.).

To minimize the impact of fluorescence and maximize sensitivity, a 785-nm excitation is used for the data collection. Laser power was set at 500 mW.

A fiber-optic superhead probe ex Horiba is used. An exposure time of 1 sec is used to obtain a good quality signal.

A liquid detergent composition with a concentration of 20.77% Linear Alkyl Benzene Sulphonic Acid is produced and pumped through the continuous system passing the sensor. A level between 20.62% and 20.80% is detected. Next the concentration of Linear Alkyl Benzene Sulphonic Acid is increased to 25.24%. After reaching steady state, a level between 25.13% and 25.38% is detected. In a final step the concentration for Linear Alkyl Benzene Sulphonic Acid is increased to 31.49%. After reaching steady state a level of 31.28% to 31.46% is detected. Detection error as such is always within 1%, which is far smaller than typical dosing variations observed in a liquid detergent production plant. Typical dosing variations in plant are +/−10%.

Example 2

Apparatus is set up in the same way as according to Example 1.

A liquid detergent composition with a concentration of 4.12% of an ethoxylated polyethylene imine (PEI600EO20) is produced and pumped through the continuous system passing the sensor. A level between 4.06% and 4.18% is detected. Next the concentration of PEI600EO20 is increased to 4.81%. After reaching steady state a level of 4.79% to 4.86% is detected.

Examples 1 and 2 both confirm that the process according to the present invention can be used to accurately measure levels of detergent ingredients in a process of manufacturing a liquid detergent composition. Furthermore, detection error in both cases is within 1.5% which is far smaller than the normal dosing error seen in a manufacturing plant of up to 10%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a liquid detergent composition comprising the steps of:
   a. flowing a liquid detergent composition through a pipe, wherein the liquid detergent composition comprises two or more detergent ingredients, wherein the two or more detergent ingredients comprise surfactant, wherein the surfactant comprises linear alkyl benzene sulphonic acid;
   b. flowing the liquid detergent composition through the pipe via a Raman Spectroscopy apparatus, wherein the Raman Spectroscopy apparatus comprises a probe, and wherein the Raman Spectroscopy apparatus periodically scans the liquid detergent composition via the probe;
   c. interpreting the scanned data to determine levels of one or more of the detergent ingredients present in the liquid detergent composition;
   d. comparing the levels of the detergent ingredients present in the liquid detergent composition to pre-determined acceptable level ranges for said ingredients;
   e. optionally adjusting the level of one or more detergent ingredients, by addition of one or more detergent ingredients to the liquid detergent composition;
   f. flowing the liquid detergent composition to where optionally one or more further process steps occur; and
   g. collecting the liquid detergent composition.

2. The process according to claim 1 wherein said process is a continuous process, a batch process, or a semi-continuous process.

3. The process according to claim 2 wherein the process is a continuous process.

4. The process according to claim 1, wherein the detergent ingredients are further selected from builders, polymers, organic solvents, water, and a mixture thereof.

5. The process according to claim 1 wherein the liquid detergent composition is flowing at rate of between about 5000 kg per hour and about 150,000 kg per hour.

6. The process according to claim 1 wherein the probe is located within the pipe, located external to the pipe of a mixture thereof.

7. The process according to claim 6 wherein the probe is located external to the pipe.

8. The process according to claim 7 wherein the probe is located external to the pipe, and wherein the pipe comprises a transparent region and wherein the probe is located adjacent to said transparent region.

9. The process according to claim 8 wherein the transparent region comprises sapphire, glass, quartz or a mixture thereof.

10. The process according to claim 1 wherein in step c the interpretation is enabled by computer software.

11. The process according to claim 1 wherein in step d the comparison is enabled by computer software.

12. The process according to claim 1 wherein in step e the optional adjustment of the level of one or more detergent ingredients occurs within 30 seconds of the formulation comparison in step d.

13. The process according to claim 12 wherein in step e the optional adjustment of the level of one or more detergent ingredients occurs within 20 seconds, of the formulation comparison in step d.

14. The process according to claim 1 wherein in step e adjustment by addition of one or more detergent ingredients to the liquid detergent composition occurs upstream of the Raman spectroscopy apparatus, downstream of the Raman spectroscopy apparatus, via a correction loop or a mixture thereof.

15. The process according to claim 1 wherein the liquid detergent composition is collected in step g in a bottle, a tub, a water-soluble unit dose article, a holding tank, or a mixture thereof.

16. The process according to claim 1 wherein the liquid detergent composition is selected from laundry detergents, fabric enhancers, hard surface cleaners, air care refreshers, dish washing detergents, and mixtures thereof.

17. The process according to claim 1 wherein the liquid detergent composition is a liquid laundry detergent composition.

* * * * *